United States Patent
Bormann et al.

(10) Patent No.: US 9,040,594 B2
(45) Date of Patent: May 26, 2015

(54) METHOD AND PLANT FOR THE PRODUCTION OF METHANOL

(75) Inventors: Andreas Bormann, Frankfurt (DE); Veronika Gronemann, Karben (DE); Rainer Morgenroth, Hattstedt (DE); Jan Hagemann, Giessen (DE); Holger Schlichting, Hofheim (DE); Philipp Marius Hackel, Usingen (DE)

(73) Assignee: AIR LIQUIDE GLOBAL E&C SOLUTIONS GERMANY GMBH, Frankfurt (DE)

( * ) Notice: Subject to any disclaimer, the term of this patent is extended or adjusted under 35 U.S.C. 154(b) by 377 days.

(21) Appl. No.: 13/386,098

(22) PCT Filed: Jul. 16, 2010

(86) PCT No.: PCT/DE2010/000828
§ 371 (c)(1), (2), (4) Date: Jan. 20, 2012

(87) PCT Pub. No.: WO2011/009437
PCT Pub. Date: Jan. 27, 2011

(65) Prior Publication Data
US 2012/0129958 A1    May 24, 2012

(30) Foreign Application Priority Data

Jul. 23, 2009 (DE) .......... 10 2009 034 551

(51) Int. Cl.
*C07C 29/152* (2006.01)
*B01J 8/00* (2006.01)

(52) U.S. Cl.
CPC .................... *C07C 29/152* (2013.01)

(58) Field of Classification Search
CPC .............. C07C 29/152; C07C 31/04
USPC .......................... 518/705; 422/187
See application file for complete search history.

(56) References Cited

U.S. PATENT DOCUMENTS

| | | | |
|---|---|---|---|
| 4,326,041 A | | 4/1982 | Baehnisch |
| 4,628,066 A | | 12/1986 | Bonnell et al. |
| 5,216,034 A | * | 6/1993 | Sie ............................ 518/706 |
| 5,472,986 A | | 12/1995 | Van Dijk |
| 5,827,901 A | | 10/1998 | Koenig et al. |

(Continued)

FOREIGN PATENT DOCUMENTS

| | | |
|---|---|---|
| DE | 1296133 B | 5/1969 |
| DE | 2934332 A1 | 3/1981 |

(Continued)

OTHER PUBLICATIONS

European Patent Office, International Search Report in International Patent Application No. PCT/DE2010/000828 (Jan. 20, 2011).

(Continued)

*Primary Examiner* — Fereydoun G Sajjadi
*Assistant Examiner* — Amy C Bonaparte
(74) *Attorney, Agent, or Firm* — Leydig, Voit & Mayer, Ltd.

(57) ABSTRACT

A method for producing methanol from a synthesis gas containing hydrogen and carbon oxides with a high content of inert components includes passing the synthesis gas through a synthesis reactor so as to catalytically convert a part of the carbon oxides to methanol. The methanol is separated from the obtained mixture from the reactor. The mixture liberated from methanol is separated into a cycle stream and a purge stream. The cycle stream is recirculated so as to form a synthesis circle and combined with a fresh gas stream including hydrogen and carbon oxides before being charged into the synthesis reactor. The purge stream is supplied to a secondary reactor so as to catalytically convert a further part of the hydrogen and carbon oxides to methanol. Further methanol is separated the obtained mixture including synthesis gas, inert components and methanol vapor.

12 Claims, 1 Drawing Sheet

(56) References Cited

U.S. PATENT DOCUMENTS

| | | | |
|---|---|---|---|
| 6,100,303 A | 8/2000 | Hirotani et al. | |
| 7,019,039 B1* | 3/2006 | Fraley | 518/700 |
| 2005/0020700 A1 | 1/2005 | Bahnisch | |
| 2005/0107482 A1* | 5/2005 | Van Egmond et al. | 518/726 |
| 2007/0225385 A1* | 9/2007 | Early | 518/705 |
| 2008/0269359 A1 | 10/2008 | Bell | |
| 2011/0065966 A1 | 3/2011 | Mueeller et al. | |

FOREIGN PATENT DOCUMENTS

| | | |
|---|---|---|
| DE | 10156092 A1 | 6/2003 |
| EP | 0790226 A | 8/1997 |
| EP | 1016643 A1 | 7/2000 |
| EP | 1819653 A1 | 8/2007 |
| WO | WO 9614279 A1 | 5/1996 |
| WO | WO 03042144 A2 | 5/2003 |
| WO | WO 2009030353 A1 | 3/2009 |

OTHER PUBLICATIONS

Ullmann's Encyclopedia of Industrial Chemistry, Sixth Edition, 1998 Electronic Release, Chapter "Methanol", Sub-chapter 5.2 "Syntesis", p. 1.

* cited by examiner

METHOD AND PLANT FOR THE PRODUCTION OF METHANOL

CROSS REFERENCE TO RELATED APPLICATIONS

This application is a U.S. National Phase application under 35 U.S.C. §371 of International Application No. PCT/DE2010/000828, filed on Jul. 16, 2010, and claims benefit to German Patent Application No. DE 10 2009 034 551.5, filed on Jul. 23, 2009. The International Application was published in German on Jan. 27, 2011 as WO 2011/009437 A2 under PCT Article 21 (2).

FIELD

This invention relates to a method for the production of methanol and to a plant for carrying out this method. In particular, the invention relates to a method for converting synthesis gas with a high content of inert components to methanol. The invention furthermore relates to a method for converting an existing plant for the production of methanol from the operation with synthesis gas low in inerts to the operation with synthesis gas rich in inerts.

BACKGROUND

Methods for the production of methanol by catalytic conversion of synthesis gas containing hydrogen and carbon oxides have long since been known to those skilled in the art. For example in Ullmann's Encyclopedia of Industrial Chemistry, Sixth Edition, 1998 Electronic Release, Chapter "Methanol", Sub-chapter 5.2 "Synthesis", a method for the production of methanol is described, which is illustrated in FIG. 1 in a schematic and simplified form. In this Figure, a synthesis gas stream containing hydrogen and carbon oxides is supplied to a compressor 2 via conduit 1 and by said compressor brought to the reaction pressure of typically 5 to 10 MPa. Compressor 2 and compressor 15 can technically be coupled with each other. Via conduit 3, the compressed synthesis gas stream is supplied to a heat exchanger 4 and in the same brought to the reaction temperature, wherein the heat exchange mostly is effected against the hot product gas stream from the synthesis reactor (not shown in FIG. 1). Via conduit 5, the preheated synthesis gas stream enters into the synthesis reactor 6, where at temperatures between 200 and 300° C. the partial conversion of hydrogen with carbon oxides is effected on a methanol synthesis catalyst, wherein a product mixture containing the synthesis gas is obtained. Via conduit 7, the product mixture is discharged from the synthesis reactor. After cooling in the heat exchanger 8, the product mixture flows through conduit 9 into the separator 10, where methanol is separated as crude methanol and supplied to the further product processing via conduit 11. The gas product obtained in the separator is discharged via conduit 12 and separated into a purge stream, which is discharged via conduit 13, and into a cycle stream, which is supplied to the cycle compressor 15 via conduit 14. Via the purge stream, inert components are discharged from the process. Via conduit 16, the cycle stream is recirculated to the synthesis reactor 6, wherein fresh synthesis gas is supplied via conduit 17 and combined with the cycle stream. The ratio of the molar flow rates of cycle stream to fresh gas stream is referred to as cycle ratio.

A more advanced, two-stage method for the production of methanol is described in EP 0 790 226 B1. The methanol is produced in a cyclic process in which a mixture of fresh and partly reacted synthesis gas first is supplied to a water-cooled reactor and then to a gas-cooled reactor, in each of which the synthesis gas is converted to methanol on a copper-based catalyst. The methanol produced in the process is separated from the synthesis gas to be recirculated, which then is countercurrently passed through the gas-cooled reactor as coolant and preheated to a temperature of 220 to 280° C., before it is introduced into the first synthesis reactor. A part of the synthesis gas to be recirculated is removed from the process as purge stream, in order to prevent that inert components are enriched within the synthesis cycle. This measure is also described in the unexamined German Patent Application DE 2934332 A1 and in the European Patent Application EP 1016643 A1.

In the two methods described above it is disadvantageous that when processing synthesis gases with a high content of inert components the cycle ratio must be increased, as due to the lower partial pressures of the reactants the conversion to methanol per passage through the synthesis reactor is lower than in synthesis gas low in inerts. This leads to an increase of the required compressor capacity and—with a given production capacity for methanol—to greater dimensions for apparatuses and conduits.

Inert components on the one hand include inorganic gas constituents such as nitrogen or inert gases, which are obtained for example from the production of synthesis gas proceeding from natural gas with corresponding constituents. Such natural gases are obtained for example from Asian deposits. On the other hand, non-converted methane, which during the gasification of natural gas can be contained in the synthesis gas product, is regarded as an inert gas in the sense of the methanol synthesis. Furthermore, a nitrogen-containing synthesis gas is obtained when the gasification of natural gas is carried out with air or air enriched with oxygen, as it is described for example in the International Patent Application WO 96/14279 A1.

The problems of processing of synthesis gases rich in inerts in the methanol synthesis have long since been known. Various technical solutions have already been proposed, which could, however, not gain acceptance due to their disadvantages.

In the unexamined German Patent Application DE 1296133 B it is proposed, for example, to treat the raw synthesis gas containing inert components such as nitrogen, methane or argon by a xylene wash, whereby distinct reductions of the contents of the inert components should be achieved. Here, it is disadvantageous that before entry into the gas scrubber the temperature of the synthesis gas must be lowered to −10 to −30° C., in order to significantly lower the partial pressures of the inert components. This results in a high loss of energy. In addition, a laden absorbent is obtained, which must be aftertreated and which contains the component xylene foreign to the process of the methanol synthesis.

A similar technical teaching can be taken from the unexamined German Patent Application DE 10156092 A1, in which it is proposed to provide an absorption stage upstream of each catalytic reaction system for producing methanol, which contains a methanol synthesis catalyst as absorbent and which is operated at a temperature which lies below the temperature for the catalytic conversion to methanol. As absorbent an auxiliary substance inherent to the process is employed, but the two above-mentioned disadvantages of a required decrease in temperature and an aftertreatment or disposal of the absorbent still exist.

A method for the production of methanol from a synthesis gas obtained from the autothermal gasification of natural gas, containing 20 to 50% each of hydrogen, carbon monoxide and methane, is described in the patent application EP 1819653 A1. There are not taken any particular measures with respect to the methane remaining in the reactor product of the methanol synthesis reactor, but the hydrogen content is increased by means of conversion, the hydrogen—possibly with the likewise produced carbon dioxide—then is separated and again charged to the methanol synthesis reactor. The partial pressures of the reactants are increased by this measure, but the cycle stream remains high due to the high content of inert components.

In general, it should therefore be noted that no satisfactory technical solution of the problem has been found so far, although the problem, as illustrated, already exists for quite some time. In addition, many of the above discussed methods aim at reducing the purge stream containing inert components by a corresponding treatment as far as possible.

SUMMARY

In an embodiment, the present invention provides a method for producing methanol from a synthesis gas containing hydrogen and carbon oxides with a high content of inert components. The method includes passing the synthesis gas through at least one synthesis reactor so as to catalytically convert a part of the carbon oxides to methanol and so as to obtain a first mixture including synthesis gas, inert components and methanol vapor. The methanol is separated from the obtained first mixture so as to form a second mixture liberated from the methanol. The second mixture is separated into a cycle stream and a purge stream. The cycle stream is recirculated so as to form a synthesis circle and combined with a fresh gas stream including hydrogen and carbon oxides before being charged into the at least one synthesis reactor. The purge stream is supplied to a secondary reactor so as to catalytically convert a further part of the hydrogen and carbon oxides to methanol so as to obtain a third mixture including synthesis gas, inert components and methanol vapor. Further methanol is separated from the obtained third mixture.

BRIEF DESCRIPTION OF THE DRAWINGS

Exemplary embodiments of the present invention are described in more detail below and the features described and/or illustrated can be used in any combination. The description is provided with reference to the drawings, in which.

DETAILED DESCRIPTION

Figure 1:
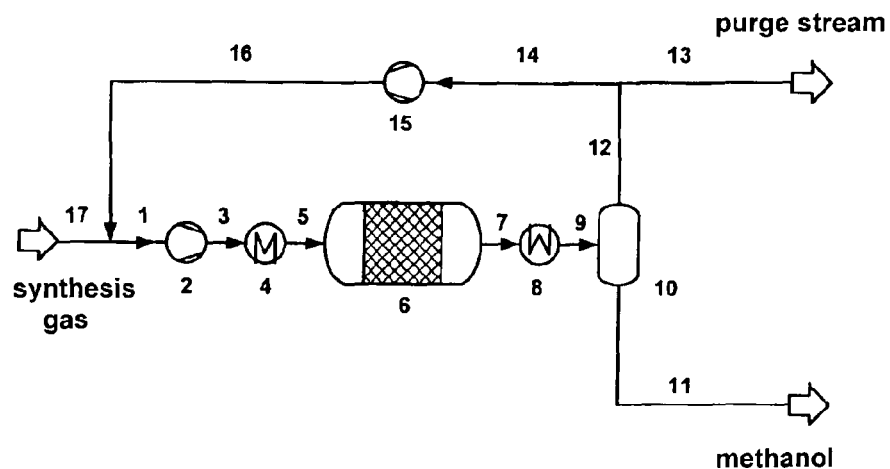
FIG. 1 schematically shows a plant for producing methanol according to a process described above, and FIG. 2 schematically shows a plant for producing methanol according to an embodiment of the present invention.

In an embodiment, the present invention avoids the above-mentioned disadvantages and provides a more economic and technically more easily feasible method for the production of methanol by using synthesis gas rich in inerts as educt gas, which in particular is characterized by a low energy demand, smaller apparatus dimensions and the avoidance of auxiliary substances foreign to the process.

In an embodiment, the invention provides an advantage to a method including the steps of:
(a) passing a synthesis gas through at least one synthesis reactor so as to catalytically convert a part of the carbon oxides to methanol and so as to obtain a first mixture including synthesis gas, inert components and methanol vapor;
(b) separating the methanol from the obtained of synthesis gas, inert components and methanol vapor;
(c) separating the mixture liberated from methanol into a cycle stream and a purge stream;
(d) recirculating the cycle stream so as to form a synthesis circle; and
(e) combining the cycle stream with a fresh gas stream including hydrogen and carbon oxides before charging the cycle stream into the at least one synthesis reactor.

In the embodiment, in order to avoid the above-mentioned disadvantages and provide a more economic and technically more easily feasible method for the production of methanol, in the method including the features (a) to (e) described above and additionally the purge stream is supplied to a secondary reactor, in which a further part of the hydrogen and the carbon oxides is catalytically converted to methanol, and from the resulting mixture containing synthesis gas, inert components and methanol vapor further methanol is separated.

For this purpose, the purge stream is compressed, brought to the reaction temperature by means of a heat exchanger or heater, and charged to the secondary reactor. With a sufficiently small pressure loss via the secondary reactor, the additional compression can also be omitted. A particularly economic configuration of the method is achieved when heating the purge stream to the reaction temperature is effected by heat exchange against the hot reaction mixture before entry into the synthesis reactor or against the hot product mixture after exit from the synthesis reactor. The heat thereby is retained in the system and utilized for the necessary heating of the gas stream to the required reaction temperature in the secondary reactor.

In the secondary reactor, the conversion of a further part of the hydrogen left in the purge stream and of the carbon oxides to methanol is effected on a catalyst active for the methanol synthesis. There can be used commercially available copper-based methanol synthesis catalysts.

In accordance with a preferred aspect of the invention it is provided to choose the ratio of cycle stream to fresh gas stream (cycle ratio) smaller than in a method for the production of methanol known per se with the features (a) to (e) described above. With a defined fresh gas stream—equivalent to a defined synthesis gas processing capacity—this corresponds to a reduction of the cycle stream and thus to a reduction of the required apparatus and conduit dimensions in the synthesis cycle, and of the required compressor capacity. The space time yield of methanol in the synthesis cycle is deteriorated thereby; surprisingly, however, this deterioration is overcompensated by the additional synthesis gas conversion in the secondary reactor, since a considerably lower synthesis gas volume flow must be processed there. Preferably, the method is carried out with a ratio of cycle stream to fresh gas stream of 10 to 90%, particularly preferably of 50 to 80%, of that of a method for the production of methanol with the features (a) to (e) described above.

Advantageously, the ratio of cycle stream to fresh gas stream (cycle ratio) can be controlled in dependence on the content of inert components in the fresh gas stream. This can be effected such that when operating the method with a defined fresh gas stream, a high cycle ratio initially is chosen. It may be advantageous to wholly or partly bypass the secondary reactor by means of a bypass conduit. Only when a significant concentration of inert components is built up in the synthesis cycle, which can be detected by a suitable analysis method, will the cycle ratio be reduced and will the purge stream charged to the secondary reactor be increased. A tracking of the cycle ratio also can be expedient with a successive deactivation of the catalyst in the synthesis reactor.

In accordance with a development of the invention, the gas stream containing the inert components and non-converted synthesis gas, which is left after the methanol separation, is removed from the process—possibly after an aftertreatment. With a high content of methane and still significant contents of hydrogen and carbon monoxide, the gas stream can be supplied to the further material or thermal use, for example as heating gas.

In accordance with a preferred aspect of the invention, the methanol obtained by catalytic conversion in the secondary reactor is supplied to the further product processing separately or, particularly preferably, along with the methanol separated from the product mixture of the synthesis reactor. The processing of the crude methanol obtained in this way to pure methanol is effected in a manner known per se by multistage distillation or rectification.

Both the synthesis reactor(s) and the secondary reactor can be operated in a water-cooled, gas-cooled or adiabatic manner. In a preferred embodiment of the method, the first synthesis reactor in the first synthesis cycle is operated in a water-cooled manner and the second synthesis reactor is operated in a gas-cooled manner. When using water-cooled reactors, the typically generated medium-pressure vapor can be used for compression or heating purposes.

The invention also extends to a plant for producing methanol from a synthesis gas containing hydrogen and carbon oxides with a high content of inert components, which is suitable for carrying out the method described above. The plant comprises one or more synthesis reactors in which a part of the carbon oxides is catalytically converted to methanol, a separator for separating the methanol from the synthesis gas, conduits for recirculating a synthesis gas cycle stream to the at least one synthesis reactor, conduits for discharging a purge stream, and a conduit for supplying a fresh gas stream of synthesis gas; it is characterized by a secondary reactor connected with a conduit for discharging the purge stream, in which a further part of the hydrogen and the carbon oxides is catalytically converted to methanol, and a separator for separating further methanol from the mixture containing synthesis gas, inert components and methanol vapor, which is contained in the secondary reactor.

The invention furthermore relates to a method for converting an existing plant for producing methanol according to a process according to features (a) to (e) of claim 1 from the operation with synthesis gas low in inerts to the operation with synthesis gas rich in inerts, in particular for carrying out the above-described process according to the invention after such conversion. The method for converting the plant is characterized in that downstream of the purge stream a secondary reactor is provided, from whose product mixture further methanol is separated, and that the plant is operated with a ratio of recirculated synthesis gas stream to fresh gas stream which is smaller than in operation of the plant with synthesis gas low in inerts.

Figure 2:
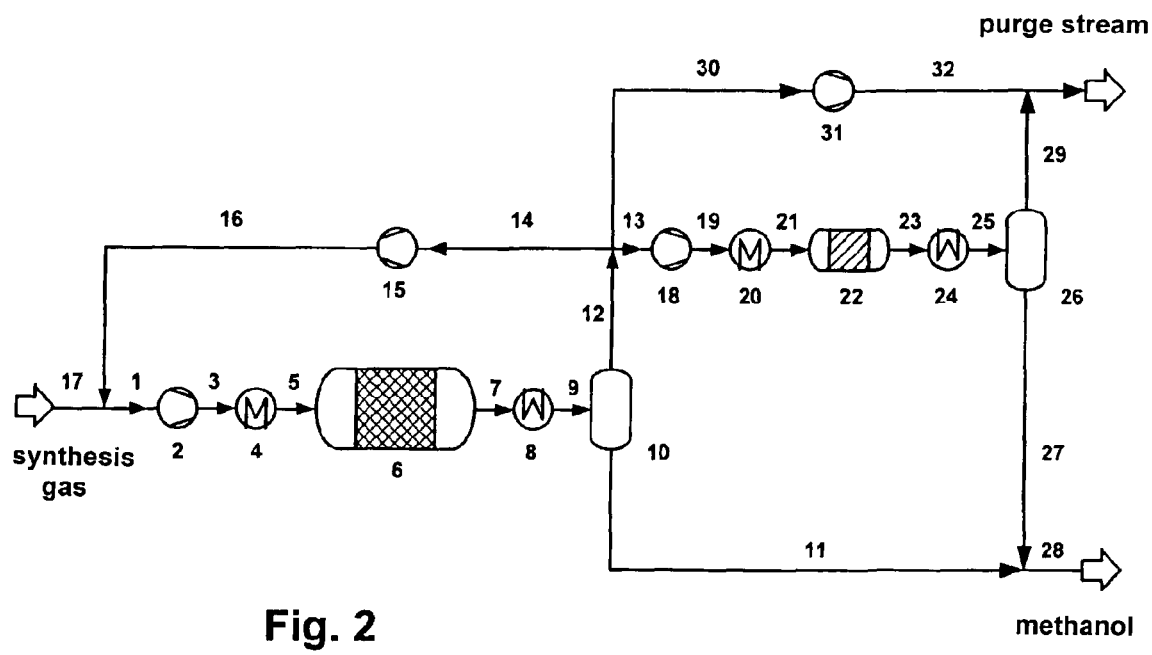

In the plant shown in FIG. 2, a mixture of fresh and recirculated synthesis gas is supplied through a conduit 1 to a compressor 2 and by said compressor brought to the reaction pressure of typically 5 to 10 MPa. Via conduit 3, the compressed synthesis gas stream is supplied to a heat exchanger 4 and in the same brought to the reaction temperature, wherein the heat exchange preferably is effected against the hot product gas stream from the synthesis reactor. Via conduit 5, the preheated synthesis gas stream enters into the synthesis reactor 6, where at temperatures between 200 and 300° C. the partial conversion of hydrogen with carbon oxides (synthesis gas) is effected on a methanol synthesis catalyst, wherein a product mixture is obtained which contains methanol, water and synthesis gas. As methanol synthesis catalyst a commercially available copper-based catalyst is used. The space velocity in the synthesis reactor typically is 10000 to 30000 $h^{-1}$. Via conduit 7, the product mixture is discharged from the synthesis reactor. After cooling in the heat exchanger 8, the product mixture flows through conduit 9 into the separator 10, where methanol is separated as crude methanol and supplied to the further product processing via conduits 11 and 28. Such product processing can be effected in a known manner, by distillation or rectification. The gas product obtained in the separator is discharged via conduit 12 and separated into a purge stream, which is discharged via conduit 13, and a cycle stream, which is supplied to the cycle compressor 15 via conduit 14. Via conduit 16, the cycle stream is recirculated to the synthesis reactor 6, wherein fresh synthesis gas is supplied via conduit 17 and combined with the cycle stream.

Via a compressor 18, the purge stream discharged via conduit 13 is compressed to a reaction pressure of 0.5-2 MPa above the mean reaction pressure of the synthesis cycle. Via conduit 19, the purge stream subsequently is supplied to a heat exchanger 20 and heated to a reactor inlet temperature of 190 to 250° C. Via conduit 21, it is supplied to the secondary reactor 22. In the secondary reactor, a commercially available copper-based catalyst also is used as methanol synthesis catalyst. The space velocity in the secondary reactor typically is 5000 to 15000 h-1. The product mixture exits from the reactor and is supplied via conduit 23 to the heat exchanger 24, where cooling is effected to temperatures distinctly below the dew point of methanol and water, preferably between 30 and 60° C. After cooling in the heat exchanger 24, the product mixture flows through conduit 25 into the separator 26, where methanol is separated as crude methanol and supplied via conduit 27 along with the methanol product of the synthesis reactor supplied via conduit 11 to the further product processing via conduit 28. The gas product obtained in the separator is discharged via conduit 29 and after an optional aftertreatment supplied to the material or energetic utilization known per se, or discarded.

In operation of the plant with secondary reactor, which is shown in FIG. 2, the ratio of cycle stream to fresh gas stream (cycle ratio) of the synthesis cycle is lowered as compared to the operation of the plant without secondary reactor. In operation with secondary reactor, the cycle ratio preferably lies in the range from 10 to 90% of that in operation of the plant without secondary reactor. In operation with secondary reactor, the cycle ratio particularly preferably lies in the range from 50 to 80% of that in operation of the plant without secondary reactor.

To provide for an operation of the plant in which the secondary reactor is bypassed by means of a bypass, the gas product discharged from the separator 10 via conduit 12 can be removed from the process via conduits 30 and 32. Preferably, the gas product discharged via conduit 32 is combined with the gas product discharged via conduit 29 before being removed from the process. A possibly required increase in pressure can be realized via a compressor 31.

In FIG. 2, compressors are shown in the conduit paths 13, 19, 21 to the secondary reactor and in the conduit path 30, 32 of the bypass conduit. With suitable pressure conditions, however, one or both of these compressors can be replaced by control valves or blowers, in order to adjust suitable mass flows to the secondary reactor and/or to the bypass.

In operation of the plant with secondary reactor, the entire purge stream preferably is guided through conduits 13, 19, 21 to the secondary reactor, in order to optimize the methanol yield. Under particular operating conditions of the plant, such as during start-up and shut-down operations, it may however be expedient to guide only part of the purge stream via conduits 13, 19, 21 to the secondary reactor and to remove the residual purge stream from the process via conduits 30, 32. In dependence on the process conditions, these parts can be chosen variably.

With a planned material or energetic utilization of the purge stream it may be advantageous not to combine the gas bypassed around the secondary reactor via conduits 30, 32 with the gas product from the separator 26, but to process the same separately, since its content of hydrogen and carbon monoxide generally is higher than in the last-mentioned gas product.

With embodiments of the invention an economic method for the production of methanol thus is proposed, which is characterized in that it is also possible to process synthesis gases with a high content of inert components. In contrast to conventional methods, the method according to embodiments of the invention do not include substances such as absorbents, which are foreign to the process or need to be disposed of or regenerated. Further advantages include the technical simplicity, small apparatus sizes and conduit dimensions; savings of catalyst and a lower energy demand, for example for the required compressor work.

NUMERICAL EXAMPLES

The following examples serve to illustrate the economy and technical feasibility of the method, which examples clearly show the advantages of methods according to embodiments of the invention as compared to the prior art. There are indicated the relative changes for important process parameters, which are obtained when employing the method according to the invention as compared to a method according to the prior art with the same methanol production capacity. As comparative method, Example 1 employs a two-stage method for methanol production with a first, water-cooled and a second, gas-cooled methanol synthesis reactor, as is taught by EP 0 790 226 B1; the manufacturing method described there is expressly included in the present description by reference. In Example 2, a single-stage method for methanol synthesis with water-cooled reactor serves as comparative method, as it is described for example by the above-mentioned reference "Ullmann's Encyclopedia of Industrial Chemistry".

Example 1

Synthesis Cycle with Two-Stage Synthesis Reactor (Water-+Gas-Cooled)+Secondary Reactor (Water-Cooled)

| Parameter | Relative change/% |
| --- | --- |
| Cycle ratio | −31.8 |
| Specific synthesis gas demand | −1.7 |
| Compressor capacity | −5.6 |
| Heat exchanger capacity | −4.0 |
| Catalyst volume | −17.1 |

In Example 1 savings are achieved in all indicated process parameters as compared to the comparative method. While the specific synthesis gas demand slightly decreases by 1.7%, the compressor and heat exchanger capacity decrease by 5.6% and 4.0%, respectively. A distinct decrease of 17.1% can also be noted for the required catalyst volume as well as a decrease of 31.8% for the cycle ratio. This corresponds to a ratio of cycle stream to fresh gas stream of about 70% of the ratio in operation of the plant without secondary reactor according to the comparative method.

Example 2

Synthesis Cycle with Single-Stage Synthesis Reactor (Water-Cooled)+Secondary Reactor (Water-Cooled)

| Parameter | Relative change/% |
| --- | --- |
| Cycle ratio | −31.8 |
| Specific synthesis gas demand | −0.4 |
| Compressor capacity | −9.0 |
| Heat exchanger capacity | +4.9 |
| Catalyst volume | −57.6 |

In Example 2 savings are also achieved as compared to the comparative method with respect to the specific synthesis gas demand and the compressor capacity. The heat exchanger capacity on the other hand rises by 4.9%. A particularly clear saving of 57.6% is achieved with regard to the required catalyst volume. Like in the upper example, the cycle ratio is reduced by 31.8%, again corresponding to a ratio of cycle stream to fresh gas stream of about 70% of that in operation of the plant without secondary reactor according to the comparative method.

LIST OF REFERENCE NUMERALS 1 conduit
2 compressor
3 conduit
4 heat exchanger
5 conduit
6 synthesis reactor(s)
7 conduit
8 heat exchanger
9 conduit
10 separator
11-14 conduit
15 compressor
16-17 conduit
18 compressor
19 conduit
20 heat exchanger
21 conduit
22 secondary reactor
23 conduit
24 heat exchanger
25 conduit
26 separator
27-30 conduit
31 compressor
32 conduit

The invention claimed is:
1. A method for producing methanol from a synthesis gas containing hydrogen and carbon oxides with a high content of inert components, the method comprising:
(a) passing the synthesis gas through at least one synthesis reactor so as to catalytically convert a part of the carbon oxides to methanol and so as to obtain a first mixture including synthesis gas, inert components and methanol vapor;

(b) separating the methanol from the obtained first mixture so as to form a second mixture liberated from the methanol;

(c) separating the second mixture into a cycle stream and a purge stream;

(d) recirculating the cycle stream so as to form a synthesis circle;

(e) combining the cycle stream with a fresh gas stream including hydrogen and carbon oxides before charging the cycle stream into the at least one synthesis reactor;

(f) supplying the purge stream to a secondary reactor so as to catalytically convert a further part of the hydrogen and carbon oxides to methanol so as to obtain a third mixture including synthesis gas, inert components and methanol vapor; and (g) separating further methanol from the obtained third mixture, wherein the secondary reactor in (f) is arranged outside of the synthesis circle.

2. The method recited in claim 1, wherein a flow rate ratio of cycle stream to the fresh gas stream in the synthesis circle is smaller than in a method for the production of methanol with the features (a) to (e).

3. The method recited in claim 2, wherein the flow rate ratio of the cycle stream to the fresh gas stream in the synthesis circle is 10 to 90% of the amount in the method for the production of methanol with the features (a) to (e).

4. The method recited in claim 3, wherein the flow rate ratio of the cycle stream to the fresh gas stream in the synthesis circle is 50 to 80% of the amount in the method for the production of methanol with the features (a) to (e).

5. The method recited in claim 1, wherein the flow rate ratio of the cycle stream to the fresh gas stream in the synthesis circle is controlled based on the content of inert components in the fresh gas stream.

6. The method recited in claim 1 wherein the separating further methanol from the obtained third mixture in step (g) forms a fourth mixture that is removed from the process.

7. The method recited in claim 1 wherein the further methanol separated in step (g) is supplied to a further product processing.

8. The method recited in claim 1 wherein the further methanol separated in step (g) is combined with the methanol separated in step (b) before being supplied to product processing.

9. The method recited in claim 1 wherein the at least one synthesis reactor is water-cooled, gas-cooled or operated in an adiabatic manner.

10. The method recited in claim 1 wherein the at least one synthesis reactor includes first and second synthesis reactors, the first synthesis reactor being water-cooled and the second synthesis reactor being gas-cooled.

11. The method recited in claim 1 wherein the secondary reactor is water-cooled, gas-cooled or operated in an adiabatic manner.

12. A method for converting an existing plant for the production of methanol from an operation with synthesis gas low in inerts to an operation with synthesis gas rich in inerts, the method comprising:

providing a plant that performs a method including:

(a) passing a synthesis gas low in inerts and including carbon oxides and hydrogen through at least one synthesis reactor so as to catalytically convert a part of the carbon oxides to methanol and so as to obtain a first mixture including synthesis gas, inert components and methanol vapor;

(b) separating the methanol from the obtained first mixture so as to form a second mixture liberated from the methanol;

(c) separating the second mixture into a cycle stream and a purge stream;

(d) recirculating the cycle stream so as to form a synthesis circle;

(e) combining the cycle stream with a fresh gas stream including hydrogen and carbon oxides before charging the cycle stream into the at least one synthesis reactor;

providing a secondary reactor, outside of the synthesis circle, downstream of the purge stream so as to catalytically convert a further part of the hydrogen and carbon oxides to further methanol and obtain a third mixture;

separating the further methanol from the third mixture; and operating the plant with a synthesis gas rich in inerts and reducing a ratio of the recirculated synthesis gas stream to fresh gas stream compared to the existing method.

\* \* \* \* \*